United States Patent [19]

Carter, Jr. et al.

[11] Patent Number: 5,250,032

[45] Date of Patent: Oct. 5, 1993

[54] HEATER FOR IN VIVO BLOOD INFUSION

[75] Inventors: Phillip R. Carter, Jr., Decatur; Byron L. Boylston, Powder Springs, both of Ga.

[73] Assignee: SpectraLogic, Inc., Atlanta, Ga.

[21] Appl. No.: 806,368

[22] Filed: Dec. 13, 1991

[51] Int. Cl.⁵ .............................................. A61F 7/12
[52] U.S. Cl. .................................. 604/113; 392/465; 392/470; 219/535; 607/111
[58] Field of Search ........................... 604/113, 114, 4; 128/399, 400, DIG. 3; 222/146.5; 219/521, 524, 527, 535; 392/311, 314, 318, 320, 465, 470, 472, 478

[56] References Cited

U.S. PATENT DOCUMENTS

| 4,293,762 | 10/1981 | Ogawa | 219/302 |
|---|---|---|---|
| 4,384,578 | 5/1983 | Winkler | 604/114 |
| 4,532,414 | 7/1985 | Shah et al. | 219/308 |
| 5,042,455 | 8/1991 | Yue et al. | 126/263 |
| 5,108,372 | 4/1992 | Swenson | 604/113 |
| 5,125,069 | 6/1992 | O'Boyle | 128/400 X |

Primary Examiner—C. Fred Rosenbaum
Assistant Examiner—Corrine Maglione
Attorney, Agent, or Firm—Kennedy & Kennedy

[57] ABSTRACT

A heater 10 for warming blood, plasma and other solutions flowing through an intravenous tube prior to its entry into a patient. The heater has a housing that has an elongated channel 17 which extends from one end of the housing to the other and which is sized to receive and releasably hold in intimate contact an elongated portion of an intravenous tube. The channel is formed with an elongated slot 18 against which is mounted a heating element H controlled by a control circuit 30 and powered by batteries B. The control circuit may energize the heating element continuously or cyclically with a regulated pulse width modulator U1 in response to sensed temperatures.

3 Claims, 4 Drawing Sheets

HEATER FOR IN VIVO BLOOD INFUSION

TECHNICAL FIELD

This invention relates to heaters for warming blood, plasma and other intravenous solutions while being infused into patients.

BACKGROUND OF THE INVENTION

During surgery and in case of emergency, blood plasma, drugs, saline solutions and glucose are commonly infused into patients. Blood is typically stored in storage bags at a temperature of about 4° C. To infuse the blood the storage bag is suspended above the patient and gravity fed through a flexible intravenous (I.V.) tube. For years, refrigerated blood, plasma and other solutions have been infused while still cold. However, patients who receive as little as two bags of cold blood sometimes become hypothermic which causes stress as the body expends energy to heat the cold fluids, energy which would be better used in combatting infection or in repairing damaged tissue. Cold fluids, at temperatures substantially below normothermic or body temperature, can also cause patients to feel uncomfortably cold as it lowers the temperature of the tissue through which it flows.

To eliminate this problem attempts have been made to heat blood storage bags to normothermic temperature prior to use. However, because the blood travels for some time through the I.V. tube prior to entering the patient, it can cool to below normothermic temperature. This problem cannot be solved by overheating the blood since that is bio-destructive. Also, because a relatively large quantity of blood is heated at one time in the storage bag, blood temperature variances may occur within the bag. If the bag is not heated continuously during transfusion it will cool over time.

Heat exchangers have also been used which circulate refrigerated blood through heated water, as shown in U.S. Pat. Nos. 4,177,816, 4,416,280, and 4,705,508. However, because large amounts of water must be warmed by these exchangers, they are rather inefficient. Their size also often requires that they be located some distance away from patients which once again permits the blood to cool within the I.V. tube between the exchanger and the patient.

As shown in U.S. Pat. No. 4,934,336, devices with heat packs have also been employed. They however require the storage bag and I.V. tube to be meticulously wrapped and unwrapped about device. Also, being exothermically reactive, the blood flow rate effects heating which lessens effective heat control.

Another type of device, shown in U.S. Pat. No. 4,735,609, utilizes a disposable pouch having an inlet and an outlet to which I.V. tubes are coupled and a heater for heating the pouch and fluids in it. Here, however, the coupling of the I.V. tube with the pouch enables air to enter both which must be bled off. This also requires additional sterility measures to be taken.

It thus is seen that a need remains for a heater for use in vivo blood infusions by which refrigerated blood may be heated to normothermic temperature prior to entry into the patient in a more efficient and effective manner. It is to the provision of such therefore that the present invention is primarily directed.

SUMMARY OF THE INVENTION

In a preferred form of the invention, a heater for in vivo blood, plasma and IV solutions infusion comprises a housing having an elongated channel sized to receive and releasably hold in intimate contact an elongated portion of an intravenous tube. The device has electrical heating means mounted to the housing adjacent the channel for applying heat to the elongated portion of an intravenous tube held in the channel and to I.V. fluids flowing through it. The device also has means for controlling the electrical heating means.

DETAILED DESCRIPTION

Figure 3:
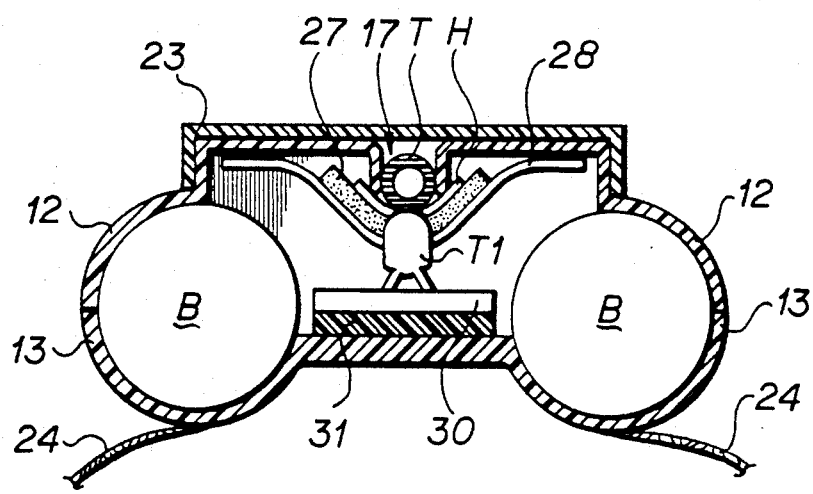
FIG. 3 is a cross-sectional view of the heater of FIG. 1.
Figure 2:
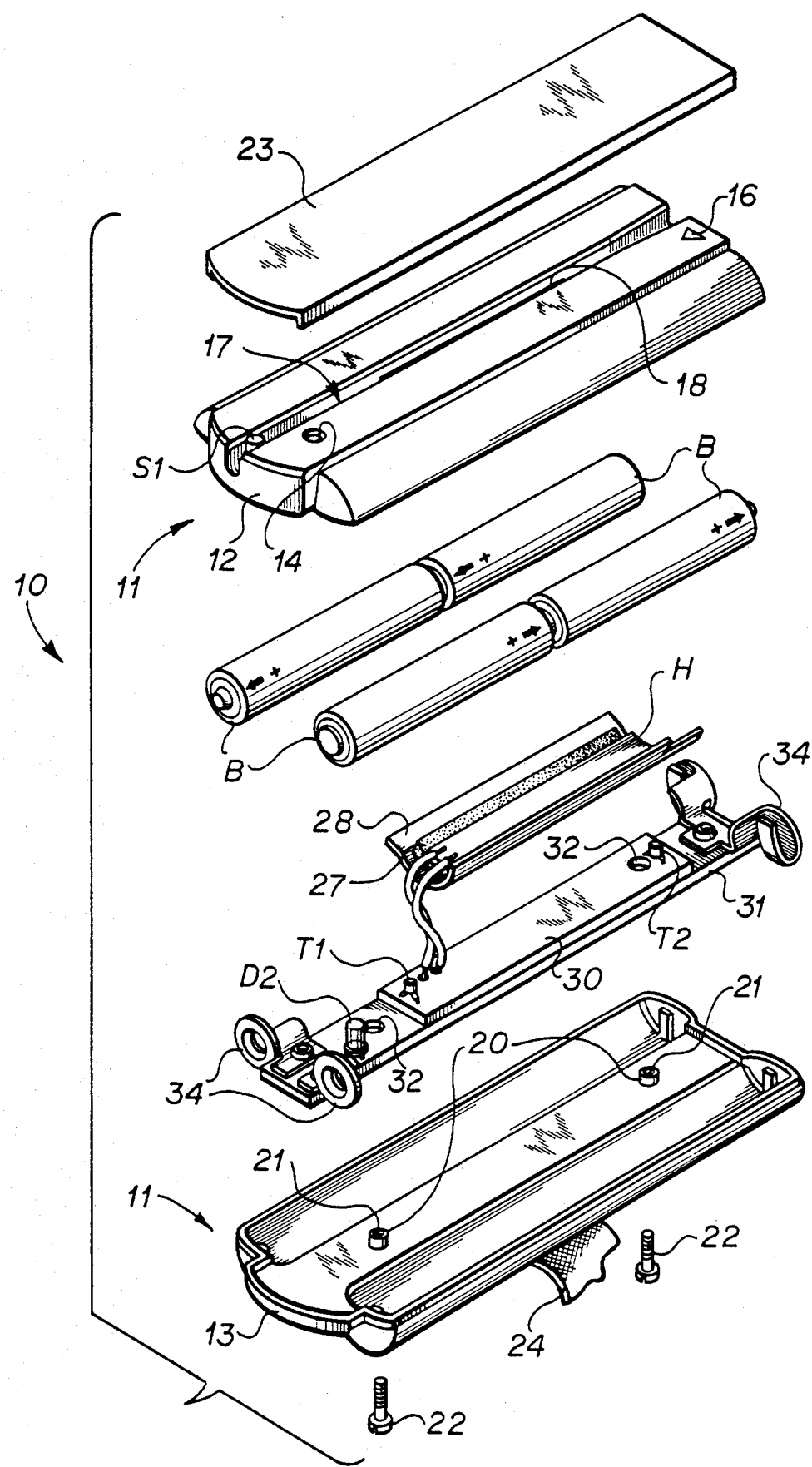
FIG. 2 is an exploded view, in perspective, of the heater of FIG. 1.

With reference next to the drawings, there is shown in FIGS. 1-4 a heater 10 for heating blood, plasma or other fluid as it is being infused into a patient. The heater has a housing 11 with an upper shell 12 and a lower shell 13. The top of the upper shell has a small opening or window 14, a flow direction indicator 16, and an elongated channel 17 that extends from one end of the housing to the other that is sized to receive and releasably hold in intimate contact an elongated portion of a conventional intravenous (I.V.) tube T. As shown in FIG. 3, the channel 17 is formed with an elongated slot 18 extending through the housing upper shell 12.

Figure 1:
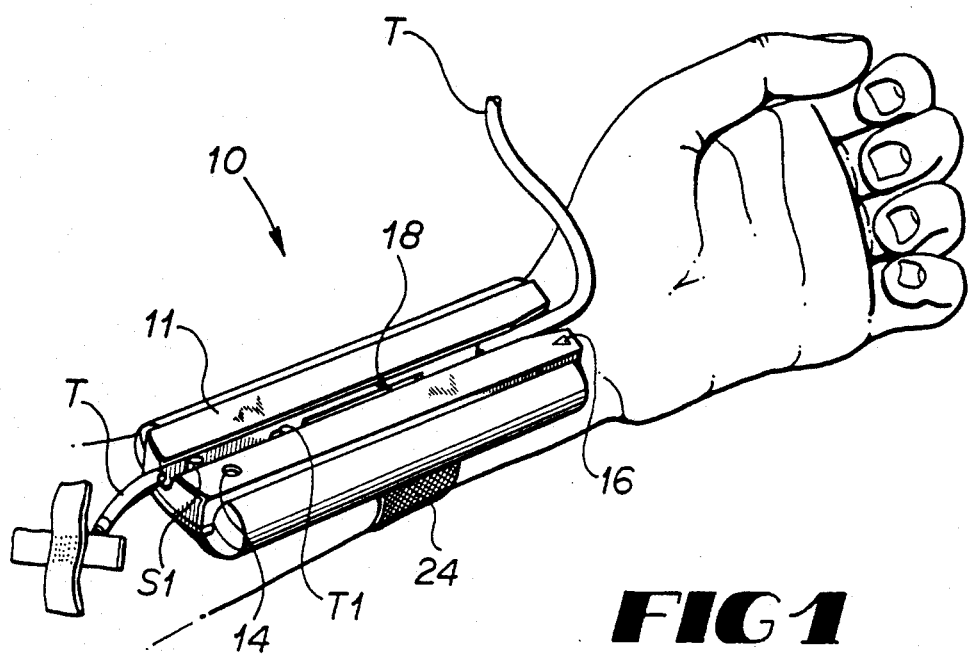
FIG. 1 is a perspective view of a heater that embodies principles of the invention in a preferred form shown strapped to the arm of a patient.

The lower shell 13 of the housing has two posts 20, each having a hole 21 extending axially therethrough and completely through the lower shell. The upper and lower shells are secured together by passing a screw 22 through each hole 21 and threading it into similar, unshown threaded posts on the upper shell 12. A transparent cap 23 is releasably mounted atop the upper shell covering the channel 17. A two-piece Velcro strap 24 is mounted to the bottom of the housing for releasably securing the heater housing to the arm of a patient, as shown in FIG. 1.

Figure 4:
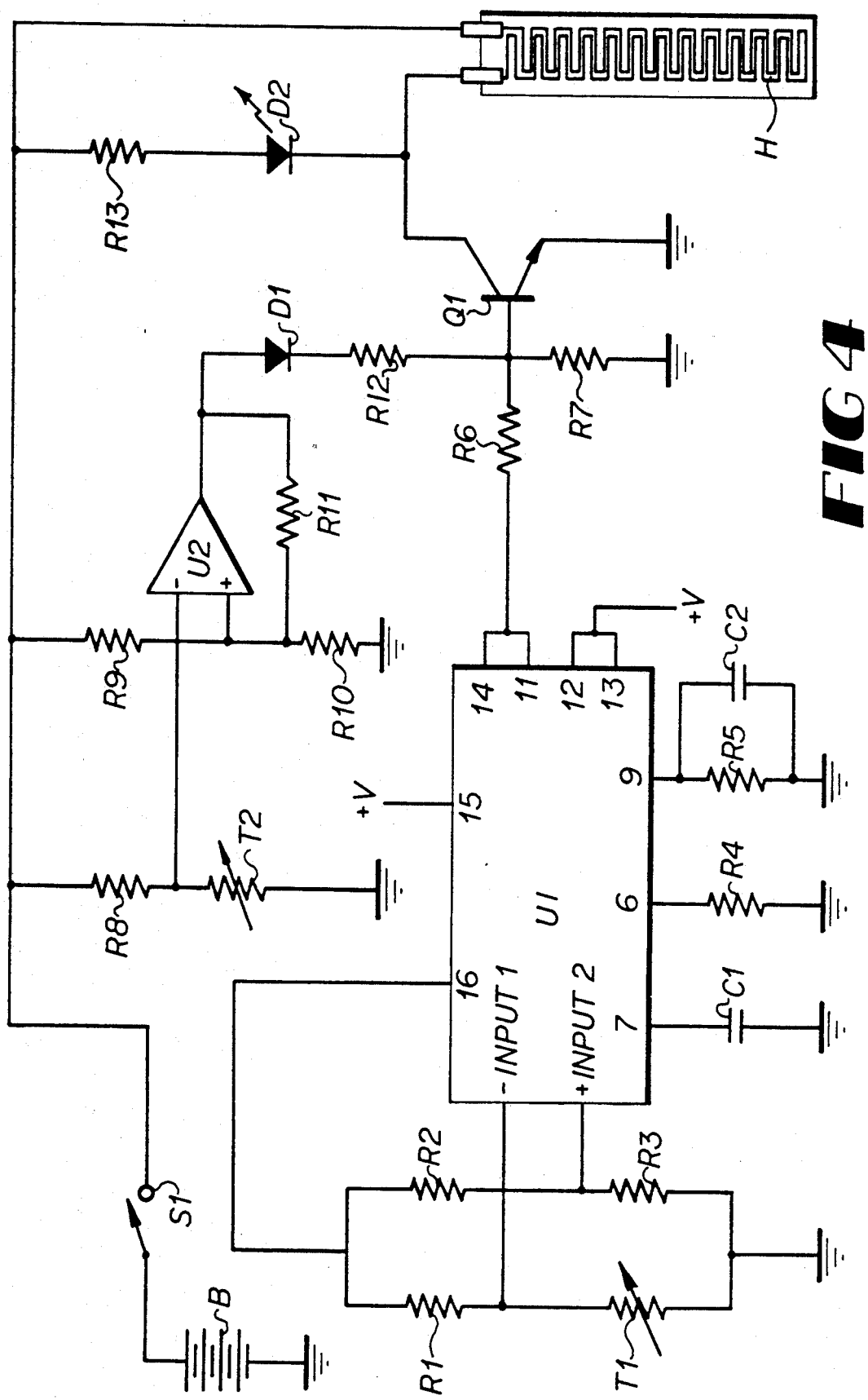
FIG. 4 is a circuit diagram of an electrical circuit of the heater of FIG. 1.

The heater 10 also has an elongated electrical heating element H mounted upon a strip of thermal insulation 27 which in turn is mounted upon a strip of adhesive foil tape 28. As best shown in FIG. 3, the foil tape 28 is mounted to the underside of the upper shell 12 with the heating element H positioned closing the bottom of the slot. Note that reference here to the heater element H being elongated refers to its overall configuration rather than to the configuration of the resistance wire itself which, as shown in FIG. 4, is serpentine.

The heating element H is electrically coupled to a control circuit indicated schematically at 30 on circuit board 31. The circuit board has mounting holes 32 sized to receive and snugly hold the posts 20 in securing it to the housing. With reference to FIG. 4, the control circuit is seen to employ a LM 3524 integrated circuit, a regulated pulse width modulator U1 and a 6 VDC power supply provided by four 1.5 VDC batteries B connected together in series. The power supply is connected through a manual off/on switch S1 directly to pins 12, 13 and 15 of the modulator, to one lead of the electrically resistive heating element H, and to its other lead through a resistor R13 and a LED lamp D2. Modulator pins 11 and 14 are connected via a current limiting resistor R6 to the base or gate of a transistor Q1 that has its collector connected to the other lead of the heating element H and its emitter grounded via resistor R7. Pin 6 of the modulator is grounded through a resistor R4 while pin 7 is connected to a grounded capacitor C1 and pin 9 is connected to ground through resistor R5 with a capacitor C2 connected across the resistor. A bridge circuit comprised of resistors R1, R2, R3 and a platinum resistive temperature detector (RTD) type temperature sensor T1 is connected across the input pins of the modulator.

The heater control circuit also has a subcircuit for accelerating heater warm-up. This is provided by a second temperature sensor T2 in the form of a NTC thermistor connected to the negative input of an operational amplifier U2 and to the batteries through resistor R8. A resistor R11 is connected across the positive input and the output of the amplifier. This output is also connected through diode D1 and current limiting resistor R12 to the base of the transistor Q1.

A representative set of values for the elements of the circuit is as follows:

| | |
|---|---|
| R1 | 2k ohms |
| R2 | 2k ohms |
| R3 | 2k ohms |
| R4 | 2.7k ohms |
| R5 | 330k ohms |
| R6 | 330 ohms |
| R7 | 10k ohms |
| R8 | 4.7k ohms |
| R9 | 47k ohms |
| R10 | 100k ohms |
| R11 | 510k ohms |
| R12 | 330 ohms |
| R13 | 3k ohms |
| H | 10 ohms |
| C1 | 0.02 uF |
| C2 | 4.7 uF |
| D1 | IN4001 |
| Q1 | ZN3507 |
| T1 | Platinum RTD |
| T2 | NTC 119 thermistor |

The control circuit 30 and heater element H are powered by four batteries B that are mounted two by two in the housing straddling the circuit board with their ends connected by resilient mounting connectors 34. The temperature sensor T1 is mounted so as to contact an I.V. tube T to sense the temperature of fluid therein. The temperature sensor T2 is mounted in contact with the housing channel 17 to sense the temperature of the channel. The LED lamp D1 is mounted adjacent the window 14 so that light emitted from it passes through the window to ambience.

Heater operation is initiated by a manual closing of switch S1 effected by insertion of the tube T into the housing channel. If the temperature sensed by T2 is below a selected value, such as 25° C., the operational amplifier gates Q1 on thereby energizing heating element H with continuous DC voltage. The amplifier effects this by input of a difference in voltage applied to its negative input by T2 and the reference voltage applied to its positive input by the voltage divider R9 and R10. Ambient noise creating high frequency oscillation near the threshold set point is prevented by R11 through which positive feedback is provided to raise and lower the threshold set point. Resistor R7 insures that Q1 is turned off completely when not gated on by U2 or the modulator.

Once the temperature sensed by T2 is raised to the selected operational level, the operational amplifier no longer operates to switch Q1 on. At this point Q1 becomes controlled exclusively by the regulated pulse width modulator U1.

The R1, R2, R3 and T1 bridge circuit provides temperature sensor input to the modulator as voltage generated by T1 responds to temperature. The positive temperature coefficient platinum sensor T1 is initially at a low value and the positive input of the modulator is at a higher potential. This causes the output of U1 to operate at a high duty cycle until its servo point is reached. Its duty cycle is then reduced to values required to maintain the device at temperature. In this manner battery life is prolonged by the batteries not being continually loaded after the initial warm-up period.

In use, as best shown in FIG. 1, an elongated portion of a conventional, flexible I.V. tube T is press fitted in the housing channel 17 into intimate contact with the on/off switch S1, the channel 17 and the heating element H. A directional indicator 16 aids in correctly positioning the I.V. tube with respect to the direction of the blood flow. The insertion of the tubing actuates the on/off switch. The cap 23 is then mounted to the housing upper shell 12 which aids in thermally insulating the tube from ambience which is firmly held in place in the channel 17.

With switch S1 now closed the temperature sensor T1 monitors the temperature of blood or plasma as it flows through the I.V. tube while temperature sensor T2 monitors the temperature the housing channel adjacent the heating element H. As previously explained, upon initial activation of the heater the temperature sensor T2 typically senses a case temperature below a selected operational level of approximately 25° C. In response, the operational amplifier U2 turns on the transistor Q1 which switches on the heater element H to which the continuous DC voltage in the applied. Once temperature sensor T2 senses that the case temperature has reached the selected operational level transistor Q1 becomes controlled solely by the modulator U1. The modulator then operates at duty cycles required to maintain temperature which can be held to within ±1° C. Capacitor C1 and resister R4 set its pulse frequency at approximately 15 Khz.

Over an extended period of time the batteries will eventually become so weak as to be unable to maintain the temperature sensed by T2 above the selected operational level. At this point Q1 once again becomes controlled by the subcircuit for accelerating heater warm-up which energizes the heating element H with a continuous voltage.

Figure 5:
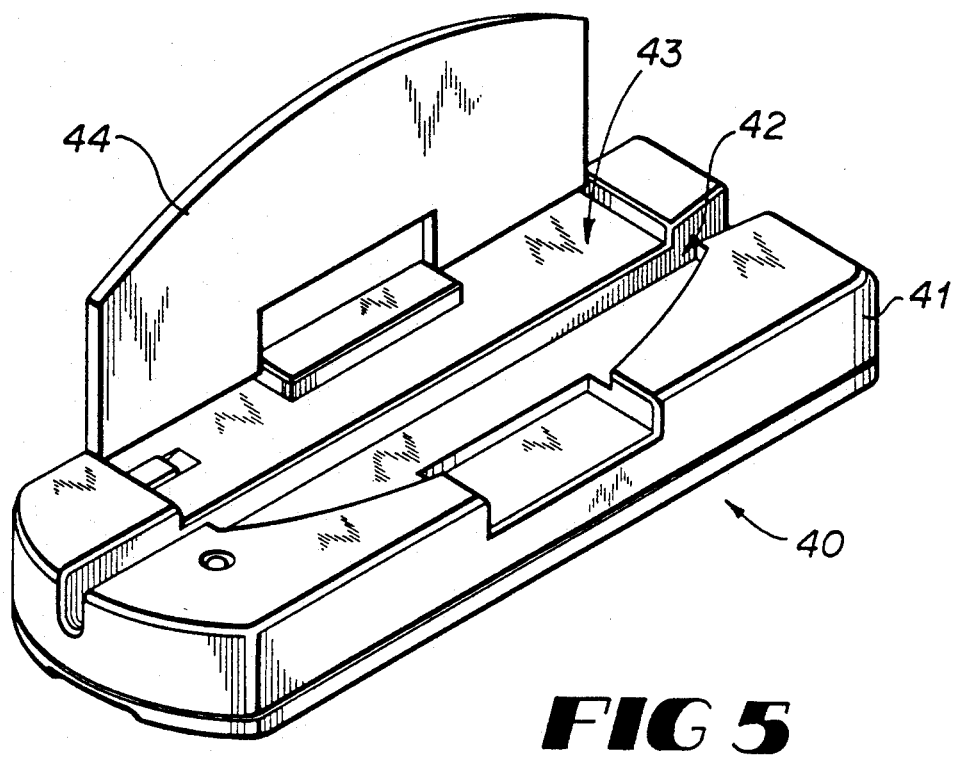
FIG. 5 in a perspective view of a heater embodying principles of the invention in another preferred form.

With reference next to FIG. 5, there is shown a heater 40 in an alternative embodiment. The heater housing 41 here has an elongated channel 42 extending from one end to the other sized to receive and releasably hold a portion of a conventional intravenous tube. The housing 41 here also has a recess 43 sized and shaped to receive a hinged cap 44. The remaining portions of the heater are essentially the same as that previously described.

Figure 6:
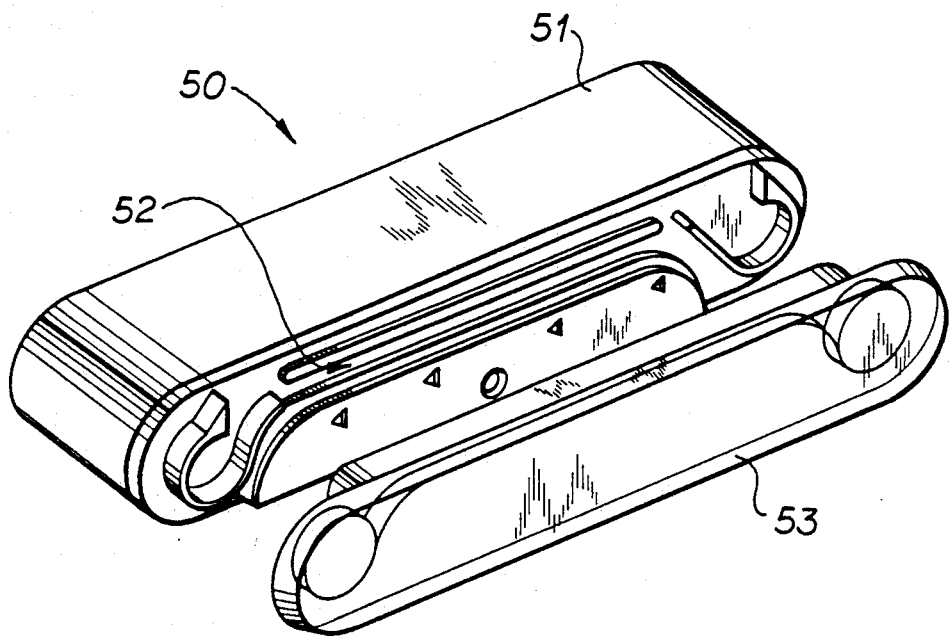
FIG. 6 in a perspective view of a heater embodying principles of the invention in yet another preferred form.

In FIG. 6 a heater 50 is shown in another alternative embodiment. The heater has a housing 51 having a U-shaped channel 52 sized to receive and releasably hold a portion of a conventional intravenous tube. The heater here has a removable cap 53 sized and shaped to be press fittedly mounted to the heater housing 51. The remaining portions of the heater are substantially the same as that previously described.

From the foregoing it is seen that a heater for warming blood and plasma or other fluids flowing through an intravenous tube is now provided which overcomes problems long associated with those of the prior art. It should however be understood that the just described embodiments merely illustrates principles of the invention in preferred forms. Many modifications, additions and deletions may, in addition to those expressly recited, be made thereto without departure from the spirit and scope of the invention as set forth in the following claims.

We claim:

1. A heater for blood, plasma and other intravenous solution infusion comprising a housing configured to be attached snugly onto the arm of a patient for the intravenous solution to exit said housing near to the point at which the intravenous solution enters the patient's body, said housing having an elongated channel sized to receive and releasibly hold in intimate contact therewith an elongated portion of a plastic intravenous tube, said channel being straddled by two elongated chambers in which batteries are mounted; electrical heating means mounted to said housing adjacent said channel and electrically coupled with said batteries for applying heat to the elongated portion of a plastic intravenous tube held in said channel and to intravenous solutions flowing therethrough; and control means for controlling power supplied by said batteries to said heater means in response to changes in temperature of intravenous solutions flowing through the elongated tube portion wherein said control means comprises means for applying continual d.c. power to said heating means at temperatures below a selected value, and means for applying pulse modulated d.c. power to said heater means at temperatures above said selected value.

2. The heater of claim 1 wherein said means for applying pulse modulated d.c. power includes sensor means for sensing the temperature of blood or plasma flowing through an intravenous tube mounted to said housing, and wherein said means for applying continual doc. power includes sensor means for sensing the temperature of said housing channel.

3. The heater of claim 1 further comprising strap means for holding said housing to a patent.

* * * * *